United States Patent [19]

Bergfeld et al.

[11] Patent Number: 5,021,603

[45] Date of Patent: Jun. 4, 1991

[54] THIURAM POLYSULFIDE PRODUCTION

[75] Inventors: Manfred Bergfeld, Erlenbach; Ludwig Eisenhuth, Obernburg; Hans-Georg Zengel, Kleinwallstadt, all of Fed. Rep. of Germany

[73] Assignee: Akzo N.V., Netherlands

[21] Appl. No.: 732,310

[22] Filed: May 9, 1985

[51] Int. Cl.$^5$ ........................................... C07C 333/00
[52] U.S. Cl. ..................................................... 558/237
[58] Field of Search ........................................ 558/237

[56] References Cited

U.S. PATENT DOCUMENTS

| | | | |
|---|---|---|---|
| 1,681,717 | 8/1928 | Whitby | 558/237 |
| 1,780,545 | 11/1930 | Whitby | 558/237 |
| 2,414,014 | 1/1947 | Cable et al. | 558/237 |
| 3,116,329 | 12/1963 | Hayes | 558/237 |
| 4,144,272 | 3/1979 | Bergomi et al. | 558/237 |
| 4,459,424 | 7/1984 | Eisenhuth et al. | 558/237 |
| 4,468,526 | 8/1984 | Eisenhuth et al. | 558/237 |

FOREIGN PATENT DOCUMENTS

| | | | |
|---|---|---|---|
| 1226564 | 10/1966 | Fed. Rep. of Germany | 558/237 |
| 2349313 | 3/1974 | Fed. Rep. of Germany | 558/237 |
| 2725165 | 1/1978 | Fed. Rep. of Germany | 558/237 |
| 2725166 | 1/1978 | Fed. Rep. of Germany | 266/455 A |
| 3105587 | 9/1982 | Fed. Rep. of Germany | 558/237 |
| 3105622 | 9/1982 | Fed. Rep. of Germany | 266/455 A |
| 1519924 | 8/1978 | United Kingdom | 558/237 |

Primary Examiner—Mary C. Lee
Assistant Examiner—Robert C. Whittenbaugh
Attorney, Agent, or Firm—Oliff & Berridge

[57] ABSTRACT

A process for the production of thiuram polysulfides substituted by aliphatic, araliphatic and/or cycloaliphatic hydrocarbon radicals is disclosed. In this process, correspondingly substituted secondary amines having a pKa value of $\geq 8$ are reacted with carbon disulfide and sulfur in a solvent at 0° to 150° C. in the presence of a metal-containing catalyst and oxygen or an oxygen-containing gas.

By virtue of its high purity, the thiuram polysulfide obtainable in this way may be directly used for its intended purpose, for example as a vulcanization accelerator or sulfur donor.

This process is particularly desirable for the substantially quantitative yields and selectivities and also for its high economy arising from the reaction being carried out in a single stage without expensive auxiliaries and from the elimination of an additional purification step.

8 Claims, No Drawings

THIURAM POLYSULFIDE PRODUCTION

BACKGROUND OF THE INVENTION

This invention relates to the production of thiuram polysulfides from secondary amines, carbon disulfide and sulfur in the presence of an oxidizing agent.

Thiuram polysulfides are used above all as sulfur donors and accelerators in the vulcanization of rubber. These compounds are marketed, for example, under the name of thiuram tetrasulfide (tetramethyl or dipentamethylene thiuram tetrasulfide) or thiuram hexasulfide (dipentamethylene thiuram hexasulfide). The exact chemical constitution of these products is not yet known because there are no analytical methods capable of distinguishing between mixtures of different polysulfides and mixtures of polysulfides and sulfur. In addition, thiuram polysulfides are sensitive compounds which, particularly in dissolved form, tend to eliminate sulfur.

These problems are described in detail, for example, in German Pat. No. 27 25 166 with reference to the example of the material known as tetramethyl thiuram tetrasulfide. By using modern analytical techniques, such as for example high pressure liquid chromatography (HPLC) and gel permeation chromatography (GPC), it can be qualitatively shown that the commercial products mentioned above are not uniform compounds, but mixtures of several polysulfides and free sulfur of which the quantitative composition varies according to the production process.

In general, processes for producing thiuram polysulfides start out from the corresponding dithiocarbamates which are normally produced from a secondary amine, carbon disulfide and an alkali or alkaline-earth hydroxide.

Thus, U.S. Pat. Nos. 1,681,717 and 1,780,545 describe a process for producing thiuram polysulfides by reacting dithiocarbamates with sulfur chlorides in accordance with the following equation:

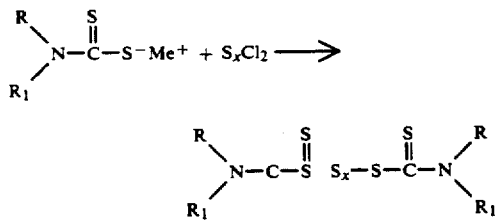

Unfortunately, the yields obtained by this process are poor. An improved process for producing thiuram tetrasulfides, particularly dipentamethylene thiuram tetrasulfide, on the basis of the above equation using sulfur monochloride is described in U.S. Pat. No. 2,414,014. Yields of up to 95% can be obtained with this process.

However, all of these processes are attended by the disadvantage that they use corrosive foul-smelling sulfur chlorides and that, in addition, large quantities of unusable salts are formed as problematical by-products.

A process which precludes the additional formation of sodium chloride is described in German Pat. No. 27 25 166. In this process, dimethylammonium dimethyldithiocarbamate is reacted with hydrogen peroxide in the presence of carbon disulfide and sulfur to form tetramethyl thiuram tetrasulfide.

In one variant of this process which is described in German Pat. No. 27 25 166, the dithiocarbamate salt to be reacted is formed in a preliminary reaction step from dimethylamine and carbon disulfide in water and the resulting aqueous solution of the dimethylammonium dimethyldithiocarbamate is subsequently further reacted in the same reaction vessel with sulfur and hydrogen peroxide to form tetramethyl thiuram tetrasulfide. Thus, according to Example 1 of German Pat. No. 27 25 166, a reaction vessel is filled with water, dimethylamine and two drops of a nonionic surfactant, the solution is stirred at 25° C. and carbon disulfide is added over a period of 14 minutes, during which the temperature rises to 35° C. The sulfur is added in one portion, followed by the addition of water. Carbon disulfide is then added at the same time as hydrogen peroxide to the suspension obtained over a period of 60 minutes, the peroxide being added 2 minutes after the beginning of the addition of carbon disulfide. The end product is ultimately obtained after filtration in a yield of 90%.

Although this process is an improvement over the first-described process, it is limited in its application to the production of tetramethyl thiuram tetrasulfide. Further disadvantages are the need to use a comparatively expensive and non-selective oxidizing agent (hydrogen peroxide) and a nonionic surfactant, and the non-quantitative yield.

A less elaborate process for the production of thiuram disulfides by reacting secondary amines and carbon disulfide in the presence of an oxidizing agent was recently described in German patent application No. P 31 05 622.9. This process, which uses metal-containing catalysts and oxygen as the oxidizing agent, gives high yields of thiuram disulfides.

There is still a need for a simplified process for producing thiuram polysulfides in high yields from inexpensive starting compounds.

SUMMARY OF INVENTION

According to the invention, the problem arising out of this need can be solved by a process for the production of thiuram polysulfides substituted by aliphatic, araliphatic and/or cycloaliphatic hydrocarbon radicals by reacting a correspondingly solvent and in the presence of an oxidizing agent, characterized in that the reaction is carried out with a secondary amine having a pKa value of $\geq 8$ at temperatures of from 0° to 150° C., in the presence of oxygen or an oxygen-containing gas as oxidizing agent and in the presence of a metal-containing catalyst.

DETAILED DESCRIPTION OF THE INVENTION

The process according to the invention is suitable for the production of a number of very differently substituted thiuram polysulfides differing in their sulfur content.

If only a single secondary amine is used as reactant, the thiuram polysulfide obtained carries the same substituent on both nitrogen atoms. If two different secondary amines are used as reactants, thiuram polysulfides containing two differently substituted nitrogen atoms can be obtained, depending on the reaction conditions (differences in the basicity of the amines, molar ratios, etc.). In addition, more or less large quantities of the two symmetrically substituted thiuram polysulfides may be formed as secondary products. The length of the sulfur bridge in the thiuram polysulfides is determined by the quantity of sulfur used. If, for example, 1 gram atom of sulfur is used per mole of secondary amine, the product obtained has a sulfur bridge consisting on average of 4 sulfur atoms (tetrasulfide). If 2 gram atoms of sulfur are used per mole of amine, the product obtained is on average a hexasulfide.

Any secondary amines having a pKa value of $\geq 8$ are suitable for use in the process. One such secondary amine is illustrated by the following formula

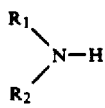

in which $R_1$ and $R_2$ may be the same or different and represent $C_{1-18}$ alkyl radicals such as, for example, methyl, ethyl, propyl, n-butyl, t-butyl, hexyl, dodecyl and octadecyl; cycloalkyl radicals, such as cyclopentyl and cyclohexyl radicals and alkylsubstituted cyclopentyl and cyclohexyl radicals; and $C_{1-18}$ alkyl radicals substituted by aryl radicals, such as phenyl and naphthyl radicals. The substituents of the secondary amine may even be attached to one another through a common bridge member. Examples of amines such as these are piperidine, pyrrolidine and derivatives thereof and also other nitrogen heterocycles.

The oxidizing agent used in the process according to the invention is oxygen or an oxygen-containing gas, particularly air.

The sulfur may be added in solid, liquid or dissolved form, for example in carbon disulfide. In this connection, it has been found that the process according to the invention involves a completely new reaction. This is because, surprisingly, a much higher oxidation rate is obtained in this reaction than in the corresponding reaction carried out without sulfur which leads to simple thiuram disulfides. This means that the sulfur has a strong accelerating effect on the oxidation.

The solvent used in the process according to the invention is not a critical factor. Thus, it is possible to use solvents of various different types, for instance aromatic hydrocarbons, such as benzene, toluene, xylene, nitrobenzene; aliphatic esters; alkyl ethers; lower alcohols, such as methanol, ethanol, isopropanol, n-propanol, n-butanol, t-butanol and amyl alcohol; chlorinated hydrocarbons, such as dichloromethane, chloroform, dichloroethane, trichloroethane; aprotic solvents, such as sulfoxide and hexamethyl phosphoric acid triamide; and also water or mixtures of the above-mentioned solvents.

In individual cases, high yields and selectivities may be obtained in pure water, depending on the secondary amine used. In general, however, the reaction velocity is slower in water than in the above-mentioned non-aqueous solvents. The solvents preferably used are aromatic hydrocarbons, lower alcohols containing up to 6 carbon atoms, mixtures of these solvents or mixtures of the lower alcohols with water.

Suitable metal-containing catalysts are any secondary group metals and derivatives thereof which are readily capable of changing valency. The metal-containing catalysts preferably used are cerium, manganese, copper, iron, cobalt, molybdenum or vanadium in elemental form or in the form of salts, oxides, complexes or organic compounds. Of the preferred metals and their derivatives, copper, manganese and cerium have greater catalytic activity than iron, cobalt, molybdenum and vanadium, although these metals and their derivatives are also useful oxidation catalysts.

Elemental copper is preferably used in the form of copper powder. Suitable copper compounds are any monovalent or divalent inorganic, organic, simple or complex copper salts. Examples of suitable monovalent copper salts are copper(I) chloride, bromide and iodide; adducts of these copper(I) halides with carbon monoxide; complex copper(I) salts, such as the alkali chlorocuprates; complex ammoniates of copper(I) cyanide, for example cyanocuprates such as potassium tricyanocuprate (I); double salts with copper(I) thiocyanate; copper(I) acetate; copper(I) sulfide; and complex double sulfides from copper(I) sulfides alkali polysulfides. Examples of suitable copper(II) salts are copper(II) chloride, bromide, sulfide, sulfate, nitrate, nitrite, thiocyanate, cyanide; Cu(II) salts of carboxylic acids such as copper(II) acetate; copper dithiocarbamate; and the complex ammoniates of copper(II) salts. Copper(I) oxide is another very suitable catalyst.

Examples of suitable manganese-containing catalysts are manganese powder, manganese dioxide, potassium permanganates, manganese acetate and manganese dithiocarbamates, and also the other manganese derivatives corresponding to the above-mentioned copper compounds. Examples of suitable cerium catalysts are metallic cerium, cerium dioxide, cerium(III) chloride, cerium(IV) chloride and cerium chlorocomplex salts, cerium nitrate and nitrato salts, cerium sulfate, cerium carbonate, cerium oxalate and the cerium sulfides.

Examples of iron catalysts are the known iron oxides, iron(II) and iron(III) salts and also the complex salts.

Examples of suitable vanadium catalysts are vanadium oxides, chlorides and sulfates and also the known double and complex salts.

Suitable cobalt catalysts are the known cobalt oxides, cobalt(II) salts and the complex salts.

Finally, examples of suitable molybdenum catalysts are the oxides, chlorides, sulfides and fluorides, the molybdates and also the known complex acido salts.

Mixtures of several of the above-mentioned catalysts may of course also be used.

The quantity of metal-containing catalysts required is surprisingly small and preferably amounts to between 0.01 and 5 mmoles per mole of secondary amine. Although even smaller quantities of catalyst may be used, longer reaction times have to be accepted in that case. Larger quantities of catalyst are not recommended because, in that case, the catalyst is in danger of precipitating and contaminating the reaction product.

The process according to the invention is carried out at temperatures of from 0° to 150° C., preferably at temperatures of from 20° to 90° C. Although temperatures above 90° C. increase the space-time yield, they are less preferred for reasons of safety.

The process according to the invention is preferably carried out at oxygen pressures or partial pressures of at least 0.1 bar. As expected, the reaction rate increases with increasing pressure. For reasons of safety, a pressure in the range from 1 to 10 bars is preferred.

To carry out the process, the reactants, the catalyst and the solvent may be combined in any order. The secondary amine and the carbon disulfide are generally used in a substantially stoichiometric ratio (1:1), although it is preferred to use the carbon disulfide in a slight excess (of 0.01 to 0.2 mole). The quantity of sulfur used may be varied within wide limits, depending on the end product required. The sulfur is preferably used in a quantity of from 1 to 3 gram atoms per mole of secondary amine. If 1 gram atom of sulfur is used per mole of secondary amine, a thiuram tetrasulfide is generally obtained; where 2 gram atoms of sulfur are used, the product obtained is a thiuram hexasulfide; and, where even larger quantities of sulfur are used, correspondingly higher thiuram polysulfides are formed. It is particularly preferred to use from 1 to 2 gram atoms of sulfur per mole of secondary amine.

In one embodiment of the invention, the secondary amine, the carbon disulfide, the sulfur and the metal-containing catalyst are dissolved or suspended in the solvent and reacted in the presence of oxygen or an oxygen-containing gas to form the corresponding thiuram polysulfide. It is equally possible initially to react only the carbon disulfide with the secondary amine (molar ratio 0.9 to 1.1 : 2.0 to 2.2), and then to react the reaction mixture obtained with sulfur and carbon disulfide (1.0 to 1.2 moles) in the presence of the metal-containing catalyst and oxygen or the oxygen-containing gas. It is also possible to isolate the dithiocarbamate formed as an intermediate product from secondary amine and carbon disulfide, and then to react this dithiocarbamate with carbon disulfide (molar ratio 1.0:1.0 to 1.2) and sulfur in the presence of oxygen or an oxygen-containing gas and the metal-containing catalyst. In addition, it is possible to add the secondary amine, the carbon disulfide and the sulfur into the reaction solution during the reaction.

The reaction time depends on the process conditions and on the secondary amine used. In general, it amounts to between a few minutes and several hours. Under favorable conditions in regard to temperature and oxygen pressure, the reaction time is between a few minutes and 1 hour.

The process according to the invention is readily carried out by delivering the oxygen or oxygen-containing gas under pressure onto the reaction mixture or by passing it into or through the reaction mixture under the temperature and pressure conditions indicated above. The end of the reaction (in the event of complete conversion) is easily recognized, for example when the uptake of oxygen comes to an end.

In most cases, as for example with the tetramethyl thiuram polysulfides or dipentamethylene thiuram polysulfides, the end product immediately precipitates from the reaction mixture and may be filtered off. In other cases, the desired product is obtained by cooling or concentrating the reaction mixture. Liquid products are obtained in pure form by distillation or by extraction.

In the industrial application of the process according to the invention, it is advantageous to recycle the mother liquor consisting essentially of solvent and metal-containing catalyst, there being no need always to add fresh metal-containing catalyst. For example, more than 10 reaction cycles may be carried out with the same mother liquor and with the same high yield without any apparent reduction in the catalytic activity of the mother liquor.

In the process according to the invention, substantially quantitative yields and selectivities of more than 99% may be obtained in most cases. The products are obtained in highly pure form and may generally be used for their intended purpose without purification. Providing the appropriate amount of sulfur is added, the products obtained correspond in their chemical composition to the commercially available products (for example tetramethyl or dipentamethylene thiuram tetrasulfide or dipentamethylene thiuram hexasulfide).

The single-stage process according to the invention is distinguished from the known two-stage process, in which the dithiocarbamates are first synthesized, by its economy and environmental compatibility because no auxiliaries are used. The process according to the invention has the advantage over the single-stage process for the production of tetramethyl thiuram tetrasulfide only, which is known from German Pat. No. 27 25 166, that a considerably less expensive oxidizing agent can be used in a simple reaction and that substantially quantitative yields and high selectivities are obtained.

The invention is illustrated by the following nonlimiting Examples.

EXAMPLE 1

In a 1 liter glass autoclave, equipped with a double jacket for the circulation of a heating liquid, a thermometer, a manometer and a stirrer, 25.64 g (0.8 gram atom) of sulfur and 31.2 g (0.41 mole) of carbon disulfide were added to a solution of 34.06 g (0.4 mole) of piperidine and 6.1 mg ($0.025 \times 10^{-3}$ mole) of manganese(II) acetate tetrahydrate in 300 ml of methanol. The reaction mixture was heated to 50° C., intensively stirred and placed under an oxygen pressure of 1.7 bar. Oxygen consumption was immediately recorded and an almost white, fine deposit was formed. After 30 minutes, the reaction was over (no further uptake of oxygen, change in color of the reaction solution from brown to pale yellow). The piperidine was completely reacted. The deposit formed was filtered off, washed with methanol and dried. 88.7 g of product melting at 126° to 129° C. were obtained.

The product corresponded in its composition to dipentamethylene thiuram hexasulfide.

Analysis: dipentamethylene thiuram hexasulfide $C_{12}H_{20}N_2S_8$: calculated: C 32.11%, H 4.49%, N 6.24%, S 57.15%, found: C 32.3%, H 4.5%, N 6.1%, S 56.8%, Analysis of the product by high pressure liquid chromatography showed that the contents of free sulfur and dipentamethylene thiuram disulfide in the product were both below 1%.

The mother liquor contained another 0.7 g of the product which can be isolated by concentration or by intensive cooling. Accordingly, the total yield amounted to 89.4 g, corresponding to 99.5% of the theoretical yield. The product obtained by this process corresponded as a sulfur donor to the products commercially available as dipentamethylene thiuram tetrasulfide.

EXAMPLE 2

Comparison Example

The procedure was as in Example 1, except that no sulfur was added. The uptake of oxygen was considerably slower. After a reaction time of 30 minutes, dipentamethylene thiuram disulfide melting at 132° C. was formed in a yield of only 16.2 g (corresponding to 25% of the theoretical yield). This Example shows that the sulfur greatly accelerates the reaction.

EXAMPLE 3

The procedure was as in Example 1, except that only 12.82 g (0.4 gram atom) of sulfur were used. The reaction time was 65 minutes. The product obtained melted at 124° to 127° C. and corresponded in its composition to dipentamethylene thiuram tetrasulfide.

Analysis: dipentamethylene thiuram tetrasulfide $C_{12}H_{20}N_2S_6$: calculated: C 37.46%, H 5.24%, N 7.28%, S 50.1%, found: C 37.8%, H 5.3%, N 7.3%, S 49.7%.

The free sulfur content was below 1% (high pressure liquid chromatography). The yield amounted to 88.9 g (99.0% of the theoretical yield).

EXAMPLE 4

17.03 g (0.2 mole) of piperidine, 15.96 g (0.21 mole) of carbon disulfide and 19.2 g (0.6 gram atom) of sulfur were reacted as in Example 1 in 300 ml of methanol in the presence of 6.1 mg ($0.025\times10^{-3}$ mole) of manganese(II) acetate and oxygen. The reaction temperature was 50° C., the oxygen pressure 1.7 bar and the reaction time 60 minutes.

The dipentamethylene thiuram polysulfide thus obtained melted at 112° to 120° C. and had an elemental composition of $C_{12}H_{10}N_2S_{10}$. The yield amounted to 49.83 g (97.2% of the theoretical yield).

EXAMPLES 5 to 8

The procedure was as in Example 1, except that different solvents were used. The results are shown in Table 1.

TABLE 1

| Example No. | Solvent (300 ml) | Reaction time (mins.) | Yield (% of theoretical) |
|---|---|---|---|
| 5 | ethanol | 45 | 99.2 |
| 6 | isopropanol | 65 | 99.5 |
| 7 | toluene | 220 | 96.8 |
| 8 | methanol/7.5% water | 60 | 98.7 |

EXAMPLES 9 to 12

The procedure was as in Example 1, except that other catalysts and different reaction temperatures were used. The corresponding reaction times and product yields are shown in Table 2.

TABLE 2

| Example No. | Catalyst | (mmole) | Reaction temp. (°C.) | Reaction time (mins.) | Yield (% of theoretical) |
|---|---|---|---|---|---|
| 9 | $Cu(OAc)_2H_2O$ | (0.1) | 50 | 120 | 96.5 |
| 10 | $CuSO_4$ | (0.05) | 60 | 110 | 95.8 |
| 11 | $Ce(NO_3)_3$ | (0.05) | 40 | 45 | 98.0 |
| 12 | $NH_4Ce(NO_3)_4$ | (0.02) | 50 | 35 | 97.4 |

EXAMPLE 13

In this Example, air was used as the oxygen-containing gas. 34.06 g (0.4 mole) of piperidine, 31.2 g (0.41 mole) of carbon disulfide and 25.64 g (0.8 gram atom) of sulfur were reacted as in Example 1 in 300 ml of methanol in the presence of 12.2 mg (0.05 mmole) of manganese(II) acetate and air (total pressure 5 bars). The reaction temperature was 60° C. and the reaction time 40 minutes. The dipentamethylene thiuram hexasulfide product was obtained in a yield of 88.1 g, corresponding to 98.3% of the theoretical yield.

EXAMPLES 14 to 17

In the following Examples, other secondary amines were used. In each case, the procedure adopted was as described in Example 1, the solvent used was methanol (300 ml) and the oxygen pressure was 1.7 bar.

The other reaction conditions and also the yields and melting points of the corresponding thiuram polysulfides are shown in Table 3.

TABLE 3

| Example No. | Sec. amine (mole) | $CS_2$ (mole) | Sulfur (gram atom) | Mn(II) acetate (mmole) | Reaction time (mins.) | Reaction temp. (°C.) | Product M.p. (°C.) | Yield (% of the theoretical) |
|---|---|---|---|---|---|---|---|---|
| 14 | $(CH_3)_2NH$ (0.4) | 0.41 | 0.4 | 0.025 | 95 | 50 | $((CH_3)_2NCS_2)_2S_2$ 108–127 | 97.5 |
| 15 | $(CH_3)_2NH$ | 0.41 | 0.8 | 0.025 | 50 | 50 | $((CH_3)_2NCS_2)_2S_4$ 99–104 | 98.3 |
| 16 | $(C_2H_5)_2NH$ (0.3) | 0.31 | 0.3 | 0.2 | 135 | 25 | $((C_2H_5)_2NCS_2)_2S_2$ wax-like | 94.5 |
| 17 | $(CH_2)_4\ \ NH$ (0.4) | 0.41 | 0.8 | 0.025 | 70 | 50 | $((CH_2)_4\ \ NCS_2)_2S_4$ 134–136 | 93.6 |

What is claimed is:

1. A process for the production of thiuram polysulfides substituted by at least one member selected from the group consisting of aliphatic, araliphatic and cycloaliphatic hydrocarbon radicals, comprising reacting (a) a secondary amine substituted by at least one member selected from the group consisting of aliphatic, araliphatic and cycloaliphatic hydrocarbon radicals, said secondary amine having a pKa value of $\geq 8$, (b) carbon disulfide and (c) sulfur, the reaction being carried out in a solvent at temperatures of from 0° to 150° C. in the presence of an oxidizing agent comprising oxygen or an oxygen-containing gas, and a metal-containing catalyst.

2. A process as claimed in claim 1, wherein from 1 to 1.2 moles of said carbon disulfide are used per mole of said secondary amine.

3. A process as claimed in claim 1, wherein from 1 to 3 gram atoms of said sulfur are used per mole of said secondary amine.

4. A process as claimed in claim 1, wherein said metal-containing catalyst is used in quantities of from 0.01 to 5 mmoles per mole of said secondary amine.

5. A process as claimed in claim 1, wherein said catalyst comprises at least one member selected from the group consisting of cerium, manganese, copper, iron, cobalt, molybdenum and vanadium in elemental form or in the form of salts, oxides, complexes or organic compounds.

6. A process as claimed in claim 1, wherein said solvent comprises at least one member selected from the group consisting of an optionally substituted aromatic hydrocarbon, a lower alcohol containing up to 6 carbon atoms and a mixture of the lower alcohol with water.

7. A process as claimed in claim 1, wherein the reaction is carried out at temperatures of from 20° to 90° C.

8. A process as claimed in claim 1, wherein the reaction is carried out in a single step.

* * * * *

UNITED STATES PATENT AND TRADEMARK OFFICE
CERTIFICATE OF CORRECTION

PATENT NO. : 5,021,603
DATED : June 4, 1991
INVENTOR(S) : Manfred BERGFELD et al It is certified that error appears in the above-identified patent and that said Letters Patent is hereby corrected as shown below:

Col. 2, line 44, after "correspondingly" insert --substituted secondary amine with carbon disulfide and sulfur in a--.

Col. 3, line 20, change "alkylsubstituted" to --alkyl-substituted--.

Col. 4, line 67, change "(of0.01" to --(of 0.01--.

Col. 6, lines 14-15, change "nonlimiting" to --non-limiting--.

Col. 7, in Table 3, the line for Example No. 17 should read as follows:

--17   $(CH_2)_4NH$ (cyclic)          $((CH_2)_4NCS_2)_2S_4$ (cyclic)

(.04)   0.41   0.8   0.025   70   50   134-136        93.6--

Signed and Sealed this

Eighth Day of December, 1992

*Attest:*

DOUGLAS B. COMER

*Attesting Officer*      *Acting Commissioner of Patents and Trademarks*